United States Patent [19]

Avar

[11] Patent Number: 4,916,175

[45] Date of Patent: * Apr. 10, 1990

[54] N-(2,2,6,6,-TETRAALKYLPIPERIDINYL-4)-N'-PHENYL OXALIC ACID DIAMIDES

[75] Inventor: Lajos Avar, Biel-Benken, Switzerland

[73] Assignee: Sandoz Ltd., Basel, Switzerland

[*] Notice: The portion of the term of this patent subsequent to Mar. 8, 2005 has been disclaimed.

[21] Appl. No.: 117,778

[22] Filed: Nov. 5, 1987

[30] Foreign Application Priority Data

Nov. 7, 1986 [GB] United Kingdom ................. 8626609

[51] Int. Cl.$^4$ ..................... C08K 5/34; C07D 401/12
[52] U.S. Cl. .................... 524/99; 524/102; 524/103; 546/186; 546/187; 546/188; 546/190; 546/18; 546/226; 546/224; 546/227; 252/403
[58] Field of Search .............. 524/99; 102, 103; 546/186, 187, 188, 190, 18, 226, 224, 227; 252/403

[56] References Cited

U.S. PATENT DOCUMENTS 4,730,017 3/1988 Avar ..................... 524/99
4,780,493 10/1988 Cantatore et al. .................... 524/99

FOREIGN PATENT DOCUMENTS 3613194 10/1986 Fed. Rep. of Germany .
712422 1/1980 U.S.S.R. .
8522666 9/1985 United Kingdom .
2180537 4/1987 United Kingdom .

Primary Examiner—John Kight
Assistant Examiner—Kriellion Morgan
Attorney, Agent, or Firm—Gerald D. Sharkin; Richard E. Vila; Thomas C. Doyle

[57] ABSTRACT

Compounds are provided which are useful as light stabilizers for polymeric materials and which have the formula

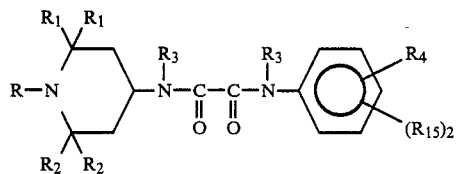

wherein $R_1$, $R_2$ and $R_4$ are organic radicals, $R_3$ and $R_{15}$ are hydrogen or organic radicals and R is hydrogen, oxygen or an organic radical.

25 Claims, No Drawings

N-(2,2,6,6,-TETRAALKYLPIPERIDINYL-4)-N'-PHENYL OXALIC ACID DIAMIDES

The invention relates to novel tetraalkylpiperidine compounds, suitable as light stabilisers in polymeric systems.

According to the invention there is provided a compound of formula I

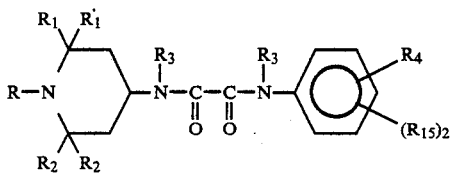

in which R is hydrogen; oxygen; $C_{1-8}$alkyl; or —$COR_5$
where $R_5$ is —$C(R_3)$=$CH_2$, $C_{1-6}$alkyl, phenyl, —CO—O—$C_{1-4}$alkyl, —$NR_7R_8$,

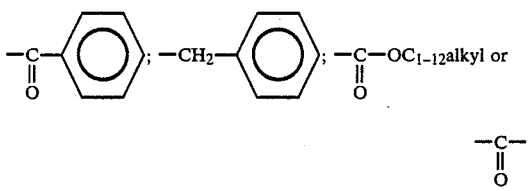

where $R_7$ is hydrogen, $C_{1-12}$alkyl, $C_{5-6}$cycloalkyl, phenyl, phenyl $C_{1-4}$alkyl or $C_{1-12}$alkylphenyl and $R_8$ is $C_{1-12}$alkyl or hydrogen, each $R_1$ independently, is —$CH_3$ or —$CH_2(C_{1-4}$alkyl) or both groups $R_1$ form a group —$(CH_2)_5$—;

each $R_2$, independently, is —$CH_3$ or —$CH_2(C_{1-4}$alkyl) or both groups $R_2$ form a group —$(CH_2)_5$—;

$R_{15}$ is hydrogen, $C_{1-12}$alkyl, $C_{1-12}$alkoxy or halogen;
each $R_3$, independently, is hydrogen or $C_{1-4}$alkyl; and $R_4$ is —OH; —O—$(CH_2)_x$—CO—$R_{10}$ or —CO—X—$R_{20}$;

where x is a number from 1 to 6 inclusive; $R_{10}$ is —O—$R_{11}$ or —$NR_3$—$R_{12}$, X is —O— or —NH— and $R_{20}$ is hydrogen or $C_{1-22}$alkyl, unsubstituted or substituted by 1 to 3 substituents (preferably 1) selected from —OH, halogen or $C_{1-4}$alkoxy;

where $R_{11}$ is $C_{1-12}$alkyl unsubstituted or monosubstituted by —OH,

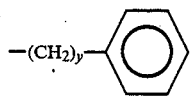

or phenyl or $R_{11}$ is a group of formula (a)

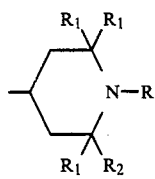

where y is an integer from 1 to 3 inclusive; and $R_{12}$ is $C_{1-12}$alkyl or a group of formula a defined above.

Preferably R is R' where R' is hydrogen, $C_{1-4}$alkyl or —CO—$R_5'$ where $R_5'$ is —CH=$CH_2$, $C_{1-4}$alkyl or —CO—O$C_{1-4}$alkyl.

Preferably each $R_1$ and each $R_2$ is $CH_3$.

Preferably $R_3$ is $R_3'$ where $R_3'$ is hydrogen or methyl, more preferably hydrogen.

Preferably $R_4$ is $R_4'$ where $R_4'$ is —OH; —O—$(CH_2)_{1-3}$—CO—O—$C_{1-6}$-alkyl or COOH, more preferably $R_4$ is $R_4''$ where $R_4''$ is —OH or —O—$(CH_2)_{1-2}$—CO—OC$_{1-4}$alkyl.

In this Specification any alkyl group is preferably methyl or ethyl; preferably any alkoxy group is methoxy or ethoxy and preferably any halogen is chlorine.

In this Specification, any group capable of being linear or branched is linear or branched.

Where a symbol appears more than once in a formula, its significances are independent of one another.

Further, according to the invention, there is provided a process for preparing a compound of formula I comprising reacting a compound of formula II

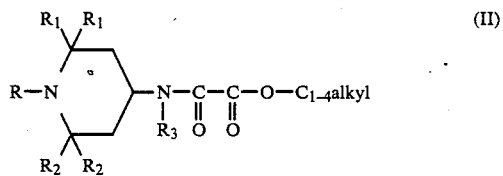

with a compound of formula III

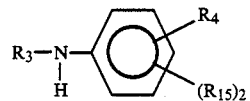

where the symbols are as defined above;
at an elevated temperature.

Preferably in the process of the invention the temperature is in the range 40° to 150° C.

Preferably the pH is 5 to 7.

Further, according to the invention there is provided a composition comprising a polymeric material and a compound of formula I defined above.

Further, according to the invention there is provided a method for stabilising a lacquer composition based on acrylic, alkyd or polyester resins (which, if desired can be crosslinked with melamine/formaldehyde resins, epoxide resins or polyisocyanates) which comprises incorporating into the resin a compound of formula I as defined above.

Further, according to the invention there is provided a lacquer composition based on acrylic, alkyd and/or polyester resins (which if desired, can be crosslinked with melamine/formaldehyde resins, epoxide resins or polyisocyanates) containing one or more compounds of formula I as defined above.

Lacquer compositions according to the invention can be metallic, one or two layer lacquer compositions or uni-one or two layer lacquer compositions. Preferably a lacquer composition according to the invention is a stoving lacquer composition.

Compounds of formula I are useful as stabilizers to protect polymeric materials against degradation by light. The compounds have particularly good solubility and miscibility in solvent systems and in liquid polymers as well as in prepolymers, which makes them useable in a wide range of polymeric materials.

The concentration of compound of formula I employed in the polymeric material is suitably 0.01 to 8% by weight, preferably 0.02% to 1% by weight. The compound may be added before, during or after the polymerization step, and may be added in solid form; in solution, preferably as a liquid concentrate containing from 20 to 80% by weight of compound of formula I; or as a solid masterbatch composition containing 20 to 80% by weight of compound of formula I and 80 to 20% by weight of a solid polymeric material which is identical with or compatible with the polymeric material to be stabilized.

Suitable polymeric materials include plastic materials for example polyethylene, polypropylene, ethylene/propylene copolymers, polyvinyl chloride, polyester, polyamide, polyurethane, polyacrylontrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastic materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottles, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples include sterically hindered phenols, sulphur or phosphorus-containing compounds or mixtures of these. Examples are benzofuran-2-ones, indolin-2-ones and sterically hindered phenols such as [-(4-hydroxy-3,5-ditert.-butylphenyl)-propionyl stearate, methane tetrakis(methylene-3(3',5'-ditert.-butyl-4-hydroxy-phenyl-)-propionate], 1,3,3-tris-(2-methyl-4-hydroxy-5-tert.-butyl phenyl)-butane, 1,3,5-tris(4-tert.-butyl-3-hydroxy-2,6-di-methylbenzyl)-1,3,5-triazin-2,4,6 (1H, 3H, 5H)-trione, bis-(4-tert.-butyl-3-hydroxy-2,6-di-methylbenzyl)dithiolterephthalate, tris(3,5-ditert.-butyl-4-hydroxy-benzyl) isocyanurate, the triester of β-(4-hydroxy-3,5-ditert.-butyl-phenyl) propionic acid with 1,3,4-tris-(2-hydroxyethyl)-5-trianzin-2,4,6 (1H, 3H, 5H)-trione, bis [3,3-bis (4'-hydroxy-3-tert.-butyl-phenyl)-butyricacid] glycol ester, 1,3,5-trimethyl-2,4,6-tris-(3,5-ditert.-butyl-4-hydroxy-benzyl) benzene, 2,2'-methylene-bis-(4-methyl-6-tert.-butylphenyl) terephthalate, 4,4-methylene-bis-(2,6-ditert.-butylphenol), 4,4'-butylidine-bis-(tert.-butyl-meta-cresol), 2,2'-methylene-bis-(4-methyl-6-tert.-butylphenol.

Sulphur containing antioxidative co-stabilizers which may be used include for example distearylthiodipropionate, di-laurylthiodipropionate, methane tetrakis (methylene-3-hexylthiopropionate), methane tetrakis (methylene-3-dodecylthiopropionate) and dioctadecyldisulphide. Phosphorus-containing co-stabilizers include for example trinoylphenyl phosphite, 4,9-distearyl-3,5,8,10-tetraoxadiphosphaspiroundecane, tris-(2,4-ditert.butylphenyl)phosphite and tetrakis (2,3-ditert.-butylphenyl)-4,4'-biphenylene diphosphonite. Further additives such as aminoaryl compounds and U.V.-absorbers and light stabilizers e.g. 2-(2'-hydroxyphenyl)-benzotriazole, 2-hydroxybenzophenone, 1,3-bis-(2'-hydroxybenzoyl)benzene, salicylates, cinnamates, benzoates and substituted benzoates, sterically hindered amines and oxalic acid diamides may be used. Other known types of additives, e.g. flame retardants and antistatic agents, may also be added.

Preferably a compound of formula XX

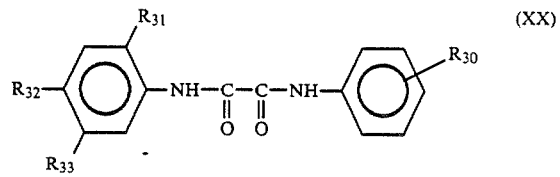

in which $R_{30}$ is $C_{6-22}$alkyl or $C_{6-22}$alkoxy;

$R_{31}$ and $R_{32}$ independently, are selected from hydrogen, $C_{1-8}$alkyl, $C_{1-12}$alkoxy, $C_{1-12}$alkylthio, phenoxy and phenylthio provided that only one of $R_{31}$ and $R_{32}$ is alkylthio, phenoxy or phenylthio; and $R_{33}$ is hydrogen or $C_{1-8}$alkyl; is added to a compound of formula I.

The compounds of the invention can also be used in photopolymeric substrates containing photoinitiators for the photopolymerisation.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 80° C., in order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment and/or metal flakes. The compounds of formula I can be in the top coat finish or the ground coat finish, preferably the former. Such two-coat metallic finishes have particular need of U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added crosslinkers, or saturated polyesters; or on self-crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2-component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates. Such polyacrylate resins are described in U.S. Pat. No. 3,062,753, the contents of which are incorporated herein by reference.

The compounds of formula I are particularly useful in acid catalysed stoving finishes particularly in the top coat of two metallic finishes.

The compounds of formula I may be added to the finish at any stage in its manufacture, and may be added in solid form or in solution, preferably in the form of a liquid concentrate in a suitable solvent or in the form of a dispersion in water or organic solvent.

In practice the compounds of formula I are added to a finish as a solution in organic solvent (as a liquid finish) in which the binder material is between 35% (low solid finishes) and 70% by weight (high solid finishes). The binder material of the finish can be in aqueous emulsion or suspension form (as an aqueous finish) in which the binder material part makes up 20 to 30% by weight. However, the compounds of formula I can be added to known powder finishes.

The compounds of formula I are to be added to the liquid or powder finishes before stoving or hardening. Preferably the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of a compound of formula I to introduce the compound of formula I to finishes for stoving.

The addition of from 0.01 to 8% by weight, preferably 0.2 to 4% by weight of one or more compounds of formula I based on the dry weight of polymer therein, gives a clear improvement in the light- and weather-stability of organic pigments in stoving finishes as well as reducing the tendency to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces. Compounds of formula III and IV can be co-polymerised with suitable monomers (particularly for those used in lacquers) e.g. acrylic based and alkyd based monomers.

The invention will now be illustrated by the following Examples in which all parts are by weight.

EXAMPLE 1

Preparation of the compound of formula 1a

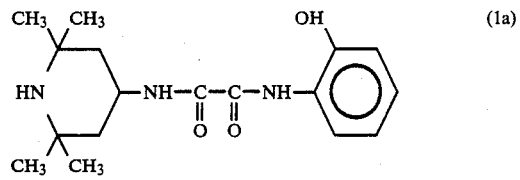

128.2 g of the compound of formula 1b

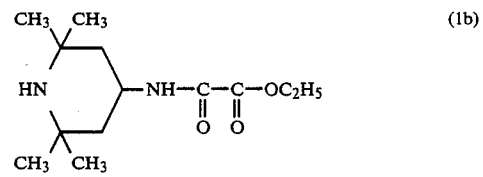

54.6 g of o-aminophenol and 1.7 g of tetrabutyl orthotitanate are stirred in 200 ml of chlorobenzene for 6 hours at 110° to 115° C. The reaction mixture is cooled to room temperature and a thick brown mass results, which is then diluted with 100 ml of acetone and vacuum dried at 10° C. The product is then washed with acetone and dried. The resulting product of formula 1a is washed with acetone and dried at 80° C. The product that results has a melting point of 216° to 218° C.

EXAMPLE 2

Preparation of a compound of formula 2a

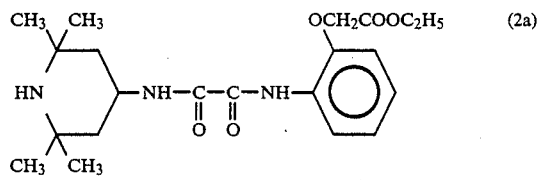

16.0 g of the compound of formula 1a (defined in Example 1), 50 ml of acetone, 12.4 g of potassium carbonate, 0.5 g of potassium iodide and 6.75 g of the ethyl ester of glacial chloroacetic acid are stirred together for 30 hours at a temperature of 50° to 52° C. The mixture is then filtered and the resulting yellow-orange solution is then concentrated. The resulting oil is then dissolved in acetone, bleached and then poured into water. The precipitate is filtered and dissolved in toluene. The solution is then poured into hexane, whereby the product precipitates out. The resulting compound of formula 2a has a melting point of 112° to 114° C.

EXAMPLES 3 and 4

The compound of formula 3a

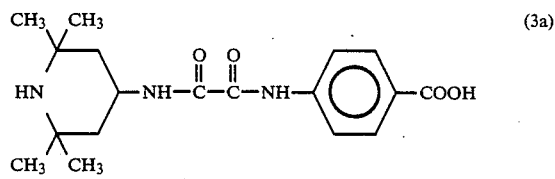

can be prepared from appropriate reactants according to the method of Example 1 or Example 2.

The compound of formula 4a

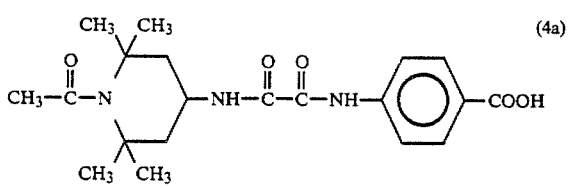

can be prepared by acylating the compound of formula 3a.

EXAMPLE 5

(a) 89.5 g of the compound of formula 5a

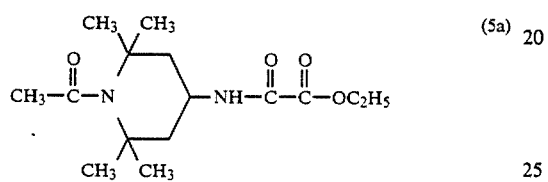

are stirred with 33.7 g of o-aminophenol and 0.5 g of boric acid in 120 ml of xylene for 6 hours at 125°–128° C. 22 ml of alcohol is distilled off and the product precipitates out in part. The product is then vacuum dried at 5° C. and the precipitate is washed with acetone and water.

A light beige powder having a melting point of 227°–229° C. result, of formula 5b

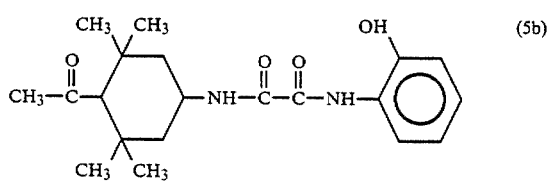

(b) the compound of formula 5c

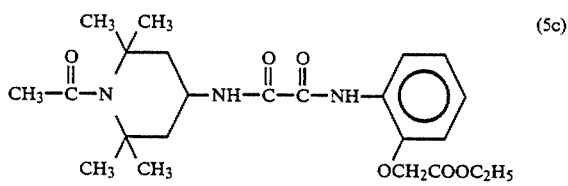

is prepared as follows:

80.9 g of the compound of formula 5b, 55.6 g of potassium carbonate and 1.0 g of potassium iodide are reacted with 30.7 g of the ethyl ester of chloroacetic acid in 450 ml of acetone at 50°–55° C. over 30 minutes. The mixture is then stirred for 6 hours until no trace of the compound of formula 5b can be detected by thin layer chromatography. The suspension is then reacted with 200 ml of toluene and 500 ml of water and then the aqueous phase is separated off. The organic phase is then washed twice with water, and then the solvent system is distilled off.

The resulting oil is crystallised out of isopropanol twice.

The resulting product of formula 5c is a white crystalline product having a melting point of 116°–117° C.

Alternatively, the compound of formula 5c can be prepared as follows:

40.5 g of the compound of formula 2a are added to 60 ml of xylene and are then reacted with 49.6 g of acetic anhydride at 50° C. The mixture is then heated to 125° C. whereby a clear solution results. The solution is then stirred for 5 hours at 125°–128° C. for five hours and then the solvent and excess acetic anhydride are distilled off under a pressure of 12 mm of Hg.

The residue that crystallises out of 100 mls of methanol is then recrystallised twice from isopropanol.

The resultant product of formula 5c has a melting point of 115°–116° C.

EXAMPLE 6

The compound of formula 6a

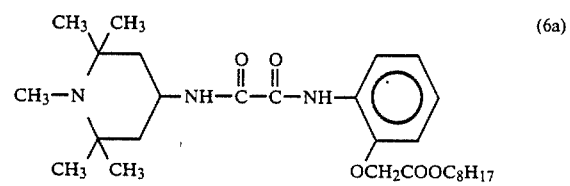

can be prepared by transesterifying the compound of formula 2a with octyl alcohol and then heating the product for 10 hours at 50° C. with ethyl iodide in the presence of $K_2CO_3$ in DMF according to the method described in Journal of Polymer Science—Polymer Chemistry Edition (1985) Vol. 23, pages 1477 to 1491.

EXAMPLES 7 to 23

The following compounds can be prepared by a method analogous to that of Example 1, 5 or 6 (where appropriate) from appropriate reactants:

EXAMPLES 7 to 10

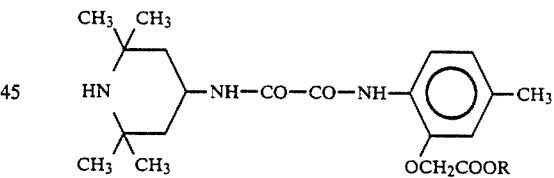

in which R is defined in Table 1 below

TABLE 1

| Ex. No. | R |
|---|---|
| 7 | $C_2H_5$ |
| 8 | $C_8H_{17}$ |
| 9 | $C_4H_9$ |
| 10 | $C_{12}H_{25}$ |

EXAMPLES 11 to 12

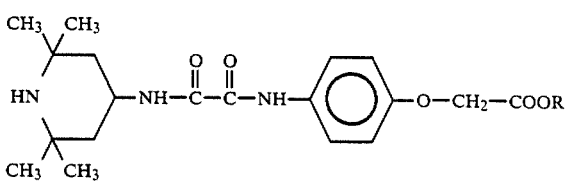

in which R is defined in Table 2 below

TABLE 2

| Ex. No. | R |
|---|---|
| 11 | $C_4H_9$ |
| 12 | $C_{12}H_{25}$ |

EXAMPLES 13 to 14

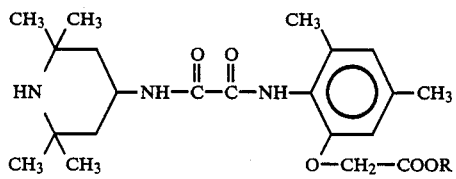

in which R is defined in Table 3 below

TABLE 3

| Ex. No. | R |
|---|---|
| 13 | $C_2H_5$ |
| 14 | $C_8H_{17}$ |
| 14a | 2,2,6,6-tetramethylpiperidyl-4 |

EXAMPLES 15 to 18

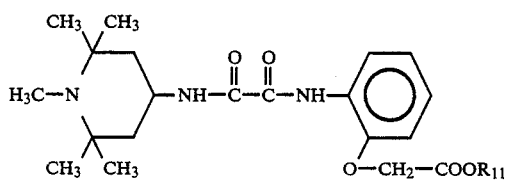

in which $R_{11}$ is defined in Table 4 below

TABLE 4

| Ex. No. | $R_{11}$ |
|---|---|
| 15 | $C_2H_5$ |
| 16 | $C_4H_9$ |
| 17 | $C_8H_{17}$ |
| 18 | $C_{12}H_{25}$ |
| 18a | 1,2,2,6,6-pentamethylpiperidyl-4 |

EXAMPLE 19

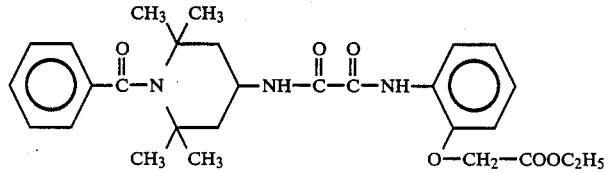

EXAMPLES 20 to 23

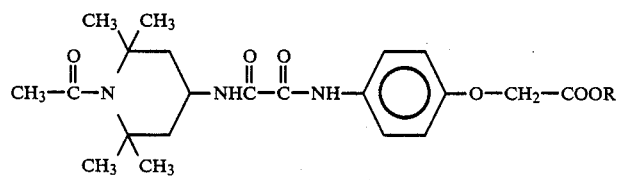

in which R is defined in Table 5 below

TABLE 5

| Ex. No. | R |
|---|---|
| 20 | $CH_3$ |
| 21 | $C_2H_5$ |
| 22 | $C_8H_{17}$ |
| 23 | $C_{12}H_{25}$ |
| 23a | 2,2,6,6-tetramethyl-1-acetylpiperidyl-4 |

APPLICATION EXAMPLE A

A clear finish of
80 Parts of Viacryl SC 344 (a 50% solution of an acryl resin from Vianova),
13.9 Parts of Maprenal MF 80 (a 72% solution of a melamine resin from Hoechst) and
4.1 Parts of Byketol OK (from Byk-Malinckrodt)
is added to 2 parts of a compound of formula 1a (described in Example 1). After 1 minute the light stabiliser material so formed is dissolved in a finish. The finish is applied conventionally (according to the known 2 layer procedure) to a metallic or single pigment finish whilst still wet by spraying to form a layer having a thickness of 30 to 40 μm. The resulting coating is then hardened at 140° for 30 minutes. The coating shows very good resistance to U.V. light and weathering.

APPLICATION EXAMPLE B

A clear finish of
29.5 Parts of Setalux C-1502 XX-60 (a 60% solution of an acryl resin from Synthese B.V.),
39.2 Parts of Setalux C-1382 BX-45 (a 45% solution of an acryl resin from Synthese B.V.),
21.4 Parts of Setamine US-138 BB-70 (a 70% solution of a melamine resin from Synthese B.V.),
2.5 Parts of Baysilonoil [(2% solution in Xylene) from Bayer] and
7.4 Parts of Depanol Y (a solvent from Hoechst)
is stirred together with 2.5 parts of a compound of formula 1a (described in Example 1) and 2 parts of an acid catalyst derived from phosphoric acid (Type: Catalyst 269-9 from American Cyanamid) to form a homogeneous mixture. The finish is applied conventionally (according to known 2 layer procedure) to a metallic or single pigment finish whilst both are still wet by spraying to form a layer having a thickness of 30 to 40 μm. The resulting coating is then hardened at 110° for 20 minutes. The coating shows very good resistance to U.V. light and weathering.

APPLICATION EXAMPLE C

A clear finish of
75 Parts Macrynal SH 510 N (a hydroxy containing acryl resin from Bayer)
2 Parts of Baysilon-oil A [(1% solution in xylene) from Bayer]
0.3 Parts of dibutyl zinc dilaurate
0.35 Parts diethanolamine
5.0 Parts of ethylglycol acetate
5.0 Parts of Solvesso 100
6.0 Parts of Xylene and
6.36 Parts of butyl acetate
is added to 2.5 parts of a compound of formula 1a (described in Example 1) and 30 parts of Desmodur N 75 (from Bayer). The homogeneous mixture so formed is applied conventionally (according to the known 2 layer procedure) to a metallic or single pigment finish whilst both are still wet by spraying to form a layer having a thickness of 30 to 40 μm and the resulting coating is hardened over 20 minutes at 80° to 90°. The resulting 2K-PUR coating shows a good resistance to U.V. light and weathering.

APPLICATION EXAMPLE D

A single white pigmented finish of
14.30 Parts of Setamine US-132 BB70 (a 70% solution of a melamine resin from Synthese)
57.15 Parts of Setal 84 W-70 (a 70% solution of an alkyd resin from Synthese)
7.70 Parts of n-butanol
1.85 Parts of butylglycol acetate
9.50 parts of Xylene and
25 Parts of titanium dioxide (Rutil type)
is added with 1.38 parts of the product of formula 1a (see Example 1). The finish is conventionally applied to a grounded steel metal to which a filler of layer thickness 20 to 30 μm has been annealed, by spraying and after standing for 30 minutes at room temperature the steel metal surface is annealed at 120° C. for 30 minutes. The resulting coating shows very good resistance to U.V. light and weathering.

In Application Examples A to D instead of the product of formula 1a, an appropriate amount of the product of any one of Examples 2 to 23 can be used.

What is claimed is:

1. A compound of formula I

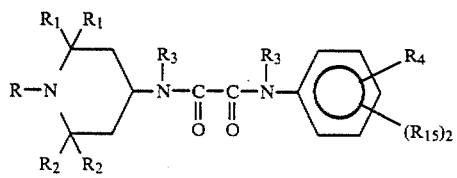

in which
R is hydrogen, oxygen, $C_{1-8}$alkyl or $-COR_5$;
each $R_1$ independently, is $-CH_3$ or $-CH_2(C_{1-4}$alkyl) or both groups $R_1$ form a group $-(CH_2)_5-$;
each $R_2$, independently, is $-CH_3$ or $-CH_2(C_{1-4}$alkyl) or both groups $R_2$ form a group $-(CH_2)_5-$;
each $R_3$, independently, is hydrogen or $C_{1-4}$alkyl;
$R_4$ is $-OH$; $-O-(CH_2)_x-CO-R_{10}$ or $-CO-X-R_{20}$;
$R_5$ is $-C(R_3)=CH_2$, $C_{1-6}$alkyl, phenyl, $-CO-O-C_{1-4}$alkyl, $-NR_7R_8$,

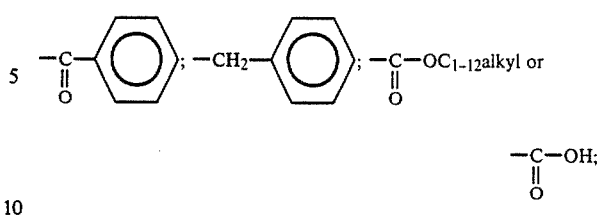

$R_7$ is hydrogen, $C_{1-12}$alkyl, $C_{5-6}$cycloalkyl, phenyl, phenyl $C_{1-4}$alkyl or $C_{1-12}$alkylphenyl;
$R_8$ is $C_{1-12}$alkyl or hydrogen;
$R_{10}$ is $-OR_{11}$ or $-NR_3-R_{12}$;
$R_{11}$ is $C_{1-12}$alkyl unsubstituted or monosubstituted by $-OH$,

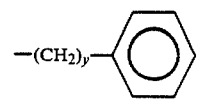

or phenyl or $R_{11}$ is a group of formula (a)

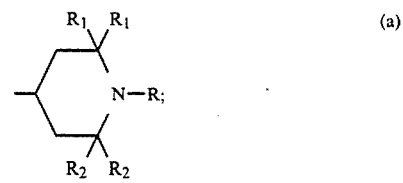

$R_{12}$ is $C_{1-12}$alkyl or a group of formula (a) defined above;
$R_{15}$ is hydrogen, $C_{1-12}$alkyl, $C_{1-12}$alkoxy or halogen;
$R_{20}$ is hydrogen or $C_{1-22}$alkyl, unsubstituted or substituted by 1 to 3 substituents selected from $-OH$, halogen and $C_{1-4}$alkoxy;
X is $-O-$ or $-NH-$;
x is a number from 1 to 6 inclusive; and
y is an integer from 1 to 3 inclusive.

2. A compound according to claim 1 wherein R is R', where R' is hydrogen, $C_{1-4}$alkyl or $-CO-R_5'$ where $R_5'$ is $-CH=CH_2$, $C_{1-4}$alkyl or $-CO-OC_{1-4}$alkyl.

3. A compound according to claim 1 wherein each $R_1$ and each $R_2$ is $CH_3$.

4. A compound according to claim 1 wherein $R_3$ is $R_3'$ where $R_3'$ is hydrogen or methyl.

5. A compound according to claim 1 wherein $R_4$ is $R_4'$ where $R_4'$ is $-OH$, $-O-(CH_2)_{1-3}CO-O-C_{1-6}$alkyl or $-COOH$.

6. A compound according to claim 1 wherein
R is R' where R' is hydrogen, $C_{1-4}$alkyl or $-CO-R_5'$;
each $R_1$ and $R_2$ is $-CH_3$;
$R_3$ is $R_3'$ where $R_3'$ is hydrogen or methyl;
$R_4$ is $R_4'$ where $R_4'$ $-OH$, $-O-(CH_2)_{1-3}CO-O-C_{1-6}$alkyl or $-COOH$;
and $R_5'$ is $-CH=CH_2$, $C_{1-4}$alkyl or $-CO-OC_{1-4}$alkyl.

7. A compound according to claim 1 of formula

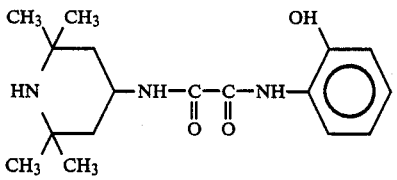

8. A compound according to claim 5 wherein $R_4$ is $R_4''$ where $R_4''$ is —OH or —O—(CH$_2$)$_{1-2}$CO—OC$_{1-4}$alkyl.

9. A compound according to claim 6 wherein $R_4$ is $R_4''$ where $R_4''$ is —OH or —O—(CH$_2$)$_{1-2}$CO—OC$_{1-4}$alkyl.

10. A process for preparing a compound according to claim 1 comprising reacting a compound of formula II

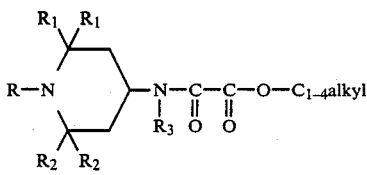

at an elevated temperature with a compound of formula III

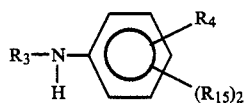

where R, $R_1$, $R_2$, $R_3$, $R_4$ and $R_{15}$ are as defined in claim 1.

11. A process for stabilizing a polymeric material against degradation by light which comprises incorporating in said polymeric material a light stabilizing-effective amount of a compound according to claim 1.

12. A composition comprising a polymeric material having incorporated therein a light stabilizing-effective amount of a compound according to claim 1.

13. A composition comprising a polymeric material having incorporated therein 0.01 to 8% by weight of a compound according to claim 1.

14. A composition comprising a polymeric material having incorporated therein 0.01 to 8% by weight of a compound according to claim 6.

15. A composition according to claim 13 wherein the polymeric material is selected from the group consisting of polyethylene, polypropylene, ethylene/propylene copolymers, polyvinyl chloride, polyester, polyamide, polyurethane, polyacrylonitrile, ABS, terpolymers of acrylates, styrene and acrylonitrile, styrene/acrylonitrile, styrene/butadiene, polybutylene, polystyrene, chlorinated polyethylene, polycarbonate, polymethylmethacrylate, polyphenylene oxide, polypropylene oxide, polyacetals, phenol/formaldehyde resins, epoxy resins and rubber.

16. A composition according to claim 14 wherein the polymeric material is selected from the group consisting of polyethylene, polypropylene, ethylene/propylene copolymers, polyvinyl chloride, polyester, polyamide, polyurethane, polyacrylonitrile, ABS, terpolymers of acrylates, styrene and acrylonitrile, styrene/acrylonitrile, styrene/butadiene, polybutylene, polystyrene, chlorinated polyethylene, polycarbonate, polymethylmethacrylate, polyphenylene oxide, polypropylene oxide, polyacetals, phenol/formaldehyde resins, epoxy resins and rubber.

17. A lacquer composition based on acrylic, alkyd and/or polyester resins containing a light stabilizing-effective amount of a compound according to claim 1.

18. A lacquer composition based on acrylic, alkyd and/or polyester resins containing a light stabilizing-effective amount of a compound according to claim 6.

19. An automotive finish comprising an organic polymer or prepolymer dissolved or dispersed in an organic solvent or in an aqueous emulsion or suspension, said finish containing a light stabilizing-effective amount of a compound of formula I according to claim 1.

20. An automotive finish comprising an organic polymer or prepolymer dissolved or dispersed in an organic solvent or in an aqueous emulsion or suspension, said finish containing a light stabilizing-effective amount of a compound of formula I according to claim 6.

21. An automotive finish according to claim 20 containing 0.01 to 8% by weight of a compound of formula I based on the dry weight of polymer therein.

22. An automotive finish according to claim 20 containing 0.2 to 4% by weight of a compound of formula I based on the dry weight of polymer therein.

23. An automotive finish comprising a solution or dispersion of an organic polymer or polymer precursor in an organic solvent and containing a light stabilizing-effective amount of a compound of formula I according to claim 1.

24. A liquid automotive finish according to claim 23 based on a combination of a melamine-formaldehyde resin with an oil-modified polyester resin, a polyacrylate resin with added crosslinkers or a saturated polyester or on a saturated polyester, or on self-crosslinked polyacrylate or polyacrylate resin copolymerized with styrene or on an aliphatic or aromatic di-iso-cyanate and a hydroxy group-containing polyacrylate, polyester or polyether resin or on thermoplastic polyacrylate resins or on polyacrylate resins with added crosslinkers in combination with melamineformaldehyde resins etherified with butanol.

25. An automotive finish according to claim 24 containing 0.01 to 8% by weight of a compound of formula I.

* * * * *